US008470372B2

(12) United States Patent
Cao

(10) Patent No.: US 8,470,372 B2
(45) Date of Patent: *Jun. 25, 2013

(54) MATERIAL WITH IMMUNOGENICITY

(75) Inventor: Yunxu Cao, Victoria (CA)

(73) Assignees: Shanghai Zerun-Ankegens Biopharmaceutical Company, Ltd., Shanghai (CN); Yunxu CAO, Victoria, BC (CA)

( * ) Notice: Subject to any disclaimer, the term of this patent is extended or adjusted under 35 U.S.C. 154(b) by 367 days.

This patent is subject to a terminal disclaimer.

(21) Appl. No.: 12/665,168

(22) PCT Filed: Jun. 18, 2008

(86) PCT No.: PCT/CN2008/071346
§ 371 (c)(1), (2), (4) Date: Dec. 17, 2009

(87) PCT Pub. No.: WO2008/154867
PCT Pub. Date: Dec. 24, 2008

(65) Prior Publication Data
US 2010/0143395 A1 Jun. 10, 2010

Related U.S. Application Data

(60) Provisional application No. 60/944,780, filed on Jun. 18, 2007, provisional application No. 60/951,856, filed on Jul. 25, 2007.

(51) Int. Cl.
*A61K 9/14* (2006.01)
*A61K 39/12* (2006.01)
*A61K 39/29* (2006.01)
*A61K 39/385* (2006.01)
*C12N 15/62* (2006.01)

(52) U.S. Cl.
USPC ............. 424/489; 424/192.1; 424/204.1; 424/227.1; 435/69.3

(58) Field of Classification Search
None
See application file for complete search history.

(56) References Cited

U.S. PATENT DOCUMENTS

| | | | |
|---|---|---|---|
| 5,667,782 A | 9/1997 | Roy | |
| 6,524,825 B1 * | 2/2003 | Mizzen et al. | 435/69.7 |
| 6,887,464 B1 | 5/2005 | Coleman et al. | |
| 6,900,035 B2 | 5/2005 | Mizzen et al. | |
| 6,962,777 B1 | 11/2005 | McCarthy et al. | |
| 7,118,754 B1 * | 10/2006 | Balloul et al. | 424/199.1 |
| 7,205,125 B2 | 4/2007 | Castillo et al. | |
| 7,217,419 B2 | 5/2007 | Wettendorff | |
| 8,088,392 B2 * | 1/2012 | Cao | 424/204.1 |
| 2006/0029612 A1 * | 2/2006 | Palmer et al. | 424/186.1 |
| 2010/0143395 A1 | 6/2010 | Cao | |

FOREIGN PATENT DOCUMENTS

| | | |
|---|---|---|
| CN | 1229437 A | 9/1999 |
| CN | 1544638 A | 11/2004 |
| CN | 1696152 A | 11/2005 |
| CN | 1824325 A | 8/2006 |
| WO | WO 02/062959 * | 8/2002 |

OTHER PUBLICATIONS

Pumpens et al (Intervirology 45:24-32, 2002).*
Devaraj, K. et al., Development of HPV Vaccines for HPV-Associated Head and Neck Squamous Cell Carcinoma. Crit Rev Oral Biol Med., Sep. 2003, vol. 14, No. 5, pp. 345-362, ISSN 1045-4411 (Identified in Information Disclosure Statement filed on Dec. 17, 2009).
Kim, D. et al., Generation and characterization of a preventive and therapeutic HPV DNA vaccine. Vaccine. Jan. 17, 2008, vol. 26, No. 3, pp. 351-360, ISSN 0264-41OX (Identified in Information Disclosure Statement filed on Dec. 17, 2009).
Tindle, R. W. et al., Chimeric Hepatitis B Core Antigen Particles Containing B- and Th-Epitopes of Human Papillomavirus Type 16 E7 Protein Induce Specific Antibody and T-Helper Responses in Immunised Mice. Virology. 1994, vol. 200, No. 2, pp. 547-557, ISSN 0042-6822 (Identified in Information Disclosure Statement filed on Dec. 17, 2009).
Kim, J. W. et al., Comparison of HPV DNA vaccines employing intracellular targeting strategies. Gene Therapy. Feb. 26, 2004, vol. 11, No. 12, pp. 1011-1018, ISSN 0969-7128 (Identified in Information Disclosure Statement filed on Dec. 17, 2009).
Devaraj, K. et al., Development of HPV Vaccines for HPV-Associated Head and Neck Squamous Cell Carcinoma. Crit Rev Oral Biol Med., Sep. 2003, vol. 14, No. 5, pp. 345-362, ISSN 1045-4411.
Kim, D. et al., Generation and characterization of a preventive and therapeutic HPV DNA vaccine. Vaccine. Jan. 17, 2008, vol. 26, No. 3, pp. 351-360, ISSN 0264-41OX.
Tindle, R. W. et al., Chimeric Hepatitis B Core Antigen Particles Containing B- and Th-Epitopes of Human Papillomavirus Type 16 E7 Protein Induce Specific Antibody and T-Helper Responses in Immunised Mice. Virology. 1994, vol. 200, No. 2, pp. 547-557, ISSN 0042-6822.
Kim, J. W. et al., Comparison of HPV DNA vaccines employing intracellular targeting strategies. Gene Therapy. Feb. 26, 2004, vol. 11, No. 12, pp. 1011-1018, ISSN 0969-7128.
International Search Report for corresponding Application No. PCT/CN2008/071346 dated Oct. 9, 2008.
Aderem et al., Nature (2000) 406:782-787.
Beames et al., Journal of Virology (1995) 69(11):6833-6838.
Bhattacharyya et al., Biochemistry (2006) 45:3069-3076.
Bhuvanakantham et al., Biochemical and Biophysical Research Communications (2005) 329:246-255.
Birnbaum et al., Journal of Virology (1990) 64(7):3319-3330.
Buckle et al., PNAS USA (1997) 94(8):3571-3575.
Burel et al., Experientia (1992) 48:629-634.
Cella et al., J. Exp. Med. (1999) 189(5):821-829.
Chackerian, Expert Rev. Vaccines (2007) 6(3):381-390.
Chatellier et al., J. Mol. Biol. (1999) 292:163-172.
Chatellier et al., J. Mol. Biol. (2000) 304:897-910.
Chatellier et al., J. Mol. Biol. (2000) 304:883-896.
Chatellier et al., PNAS USA (1998) 95(17):9861-9866.
Chen et al., J. Mol. Biol. (2001) 307:173-182.
Chromy et al., PNAS USA (2003) 100(18):10477-10482.
Cobbald et al., Journal of Virology (2001) 75(16):7221-7229.
Cristofari et al., Nucleic Acids Research (2004) 32(8):2623-2631.
De Macario et al., Biochemical and Biophysical Research Communications (2003) 301:811-812.
Deuerling et al., Critical Reviews in Biochemistry and Molecular Biology (2004) 39:261-277.
Fox et al., Protein Science (2001) 10:622-630.
Fox et al., FEBS Letters (2003) 537:53-57.

(Continued)

*Primary Examiner* — Mary E Mosher
(74) *Attorney, Agent, or Firm* — Morrison & Foerster LLP

(57) ABSTRACT

Provided is a fusion protein, which comprises human papillomavirus E7 antigen, virus capsid protein and molecular chaperone. Also provided is a macromolecule with immunogenicity aggregated by the fusion proteins. The particle morphology of the macromolecule is different from that of the virus-like particle. The macromolecule can be used for treatment of human papillomavirus relating diseases.

12 Claims, 3 Drawing Sheets

OTHER PUBLICATIONS

Friede et al., Advanced Drug Delivery Reviews (2005) 57:325-331.
Ganea, Current Protein and Peptide Science (2001) 2:205-225.
Garcea et al., Current Opinion in Biotechnology (2004) 15:513-517.
GenBank accession No. M17705.1 (1993).
GenBank accession No. K02718.1 (1994).
GenBank accession No. AF324148.1 (2005).
Grgacic et al., Methods (2006) 40:60-65.
Griffiths et al., Journal of Virology (1993) 67(7):3191-3198.
Harris et al., Immunology (1992) 77:315-321.
Hartmann et al., PNAS USA (1999) 96(16):9305-9310.
Haslbeck, Cell. Moll. Life Sci. (2002) 59:1649-1657.
Houry, Current Protein and Peptide Science (2001) 2:227-244.
Hu et al., The EMBO Journal (1997) 16(1):59-68.
Hui et al., Journal of General Virology (1999) 80:2647-2659.
Hwang et al., Arch. Virol. (1998) 143:2203-2214.
Jacobs et al., Virology (1996) 219:339-349.
Jazayeri et al., Journal of Viral Hepatitis (2004) 11:488-501.
Jewett et al., J. Mol. Biol. (2006) 363:945-957.
Kegel et al., Biophysical Journal (2004) 86:3905-3913.
Kingsman et al., Annals New York Academy of Sciences (1995) 754:202-213.
Koschel et al., Journal of Virology (1999) 73(3):2153-2160.
Krieg, Current Opinion in Immunology (2000) 12:35-43.
Levy, Methods in Enzymology (1981) 78:242-251.
Li et al., The Journal of Biological Chemistry (2005) 280(5):3400-3406.
Liang et al., Current Drug Delivery (2006) 3:379-388.
Lin et al., Cancer Research (1996) 56:21-26.
Lingappa et al., The Journal of Cell Biology (1997) 136(3):567-581.
Lingappa et al., The Journal of Cell Biology (1994) 125(1):99-111.
Linger et al., RNA (2004) 10:128-138.
Ma et al., Protein Engineering (2000) 13(9):617-627.
Macario et al., Frontiers in Bioscience (2001) 6:262-283.
Macario et al., Frontiers in Bioscience (2004) 9:1318-1332.
Macario et al., Frontiers in Bioscience (2007) 12:2588-2600.
Macario, Int. J. Clin. Lab. Res. (1995) 25:59-70.
Macario et al., J. Mol. Evol. (2006) 63:74-86.
Macario et al., Microbiology and Molecular Biology Reviews (1999) 63(4):923-967.
Macario et al., Stress (1997) 1(3):123-134.
Macejak et al., Journal of Virology (1992) 66(3):1520-1527.
Maeder et al., J. Mol. Evol. (2005) 60:409-416.
Mayer et al. in: Advances in Protein Chemistry, vol. 59, Academic Press (2002) pp. 1-44.
Mayer et al., Biol. Chem. (2000) 381:877-885.
Milich et al., Science (1986) 234(4782)1398-1401.
Morellet et al., Protein Science (2005) 14:375-386.
Mukhopadhyay et al., Journal of Virology (2002) 76(21):11128-11132.
Muriaux et al., PNAS USA (2001) 98(9):5246-5251.
Noad et al., Trends in Microbiology (2003) 11(9):438-444.
Novagen Catalogue, pET-23(+) Vector, TB064, Dec. 1998.
Ohtsuka et al., Int. J. Hyperthermia (2000) 16(3):231-245.
Paintsil et al., Virology (1996) 223:238-244.
Pattenden et al., Trends in Biotechnology (2005) 23(10):523-529.
pBluescript II Phagemid Vectors, Instruction Manual, Agilent Technologies, Inc. (2008).
Pearl et al. in: Advances in Protein Chemistry, vol. 59, Academic Press (2002) pp. 157-186.
Pumpens et al., FEBS Letters (1999) 442:1-6.
Pumpens et al., Intervirology (2001) 44:98-114.
Ramon-Luing et al., Biotechnology Letters (2006) 28:301-307.
Raychaudhuri et al., Nature Biotechnology (1998) 16:1025-1031.
Reguera et al., The Journal of Biological Chemistry (2005) 280(18):17969-17977.
Riedl et al., J. Immunol. (2002) 168:4951-4959.
Roseman et al., PNAS USA (2005) 102(44):15821-15826.
Sandovici et al., Rev. Med. Chir. Soc. Med. Nat. (1999) 103(3-4):35-43 (abstract).
Schodel et al., Intervirology (1996) 39:104-110.
Scholl et al., Journal of Controlled Release (2005) 104:1-27.
Sedlik et al., PNAS USA (1997) 94:7503-7508.
Stan et al., Biophysical Chemistry (2003) 100:453-467.
Stirling et al., EMBO Reports (2003) 4(6):565-570.
Storni et al., Advanced Drug Delivery Reviews (2005) 57:333-355.
Sullivan et al., Virology (2001) 287:1-8.
Sun et al., Cell. Mol. Life Sci. (2005) 62:2460-2476.
Taguchi et al., The Journal of Biological Chemistry (1994) 269(11):8529-8534.
Tellinghuisen et al., Journal of Virology (1999) 73(7):5309-5319.
Tellinghuisen et al., Journal of Virology (2000) 74(9):4302-4309.
Thole et al., Infection and Immunity (1987) 55(6):1466-1475.
Tsumoto et al., Protein Engineering (2003) 16(7):535-541.
Ulrich et al. in: Advances in Virus Research, vol. 50, Academic Press, New York, NY (1998) pp. 141-182.
Verdijk et al., J. Immunol. (1999) 163:57-61.
Walter, Cell. Mol. Life Sci. (2002) 59:1589-1597.
Wengler et al., Virology (1984) 132:401-412.
Weiner, Curr. Top. Microbiol. Immunol. (2000) 247:157-170.
Wilkinson et al., Biochemistry (2005) 44:2800-2810.
Xu et al., Arch. Virol. (2006) 151:2133-2148.
Yamamoto et al., Jpn. J. Cancer Res. (1994) 85:775-779.
Yang et al., Vaccine (2007) 25(22):4478-4486.
Yao et al., Journal of Virology (1996) 70(11):7910-7920.
Restriction Requirement for U.S. Appl. No. 12/140,415, mailed Feb. 16, 2010.
Response to Restriction Requirement for U.S. Appl. No. 12/140,415, filed Mar. 12, 2010.
Office Action for U.S. Appl. No. 12/140,415, mailed Apr. 19, 2010.
Response to Office Action for U.S. Appl. No. 12/140,415, filed Sep. 20, 2010.
Final Office Action for U.S. Appl. No. 12/140,415, mailed Nov. 29, 2010.
Request for Continued Examination for U.S. Appl. No. 12/140,415, filed May 26, 2011.
Notice of Allowability for U.S. Appl. No. 12/140,415, mailed Oct. 19, 2011.
Preliminary Amendment for U.S. Appl. No. 12/140,415, filed Oct. 6, 2011.

* cited by examiner

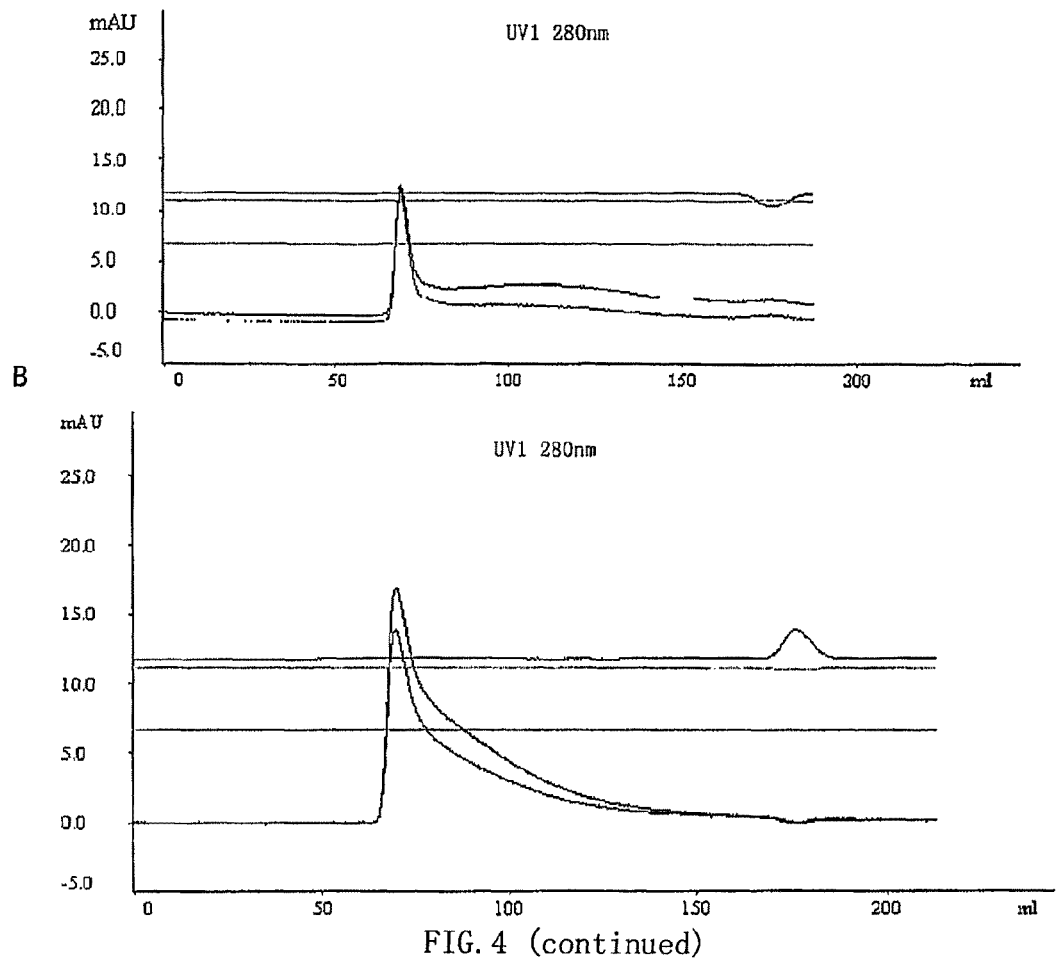
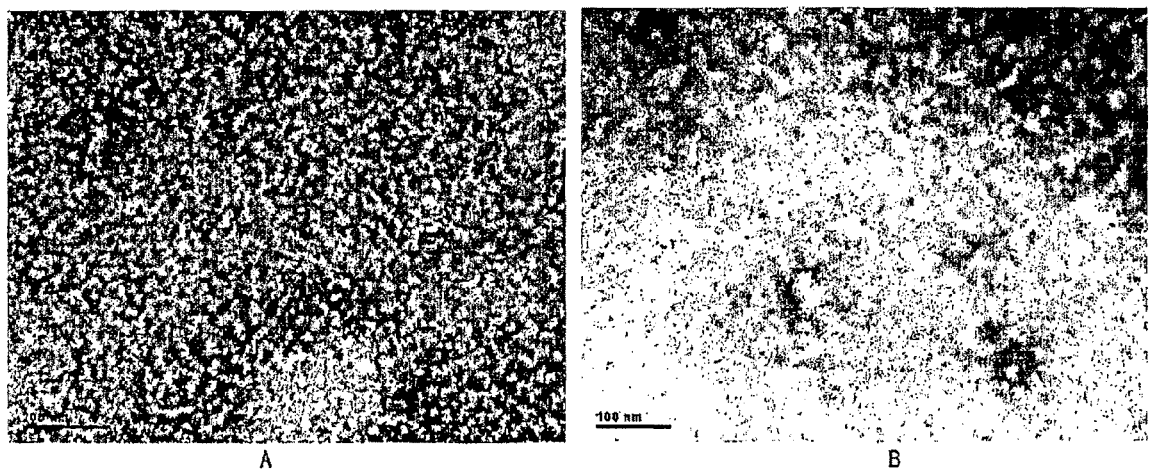
FIG. 4 (continued)
FIG. 5

SEQUENCE LISTING

<160> NUMBER OF SEQ ID NOS: 2

<210> SEQ ID NO 1
<211> LENGTH: 823
<212> TYPE: PRT
<213> ORGANISM: artificial sequence
<220> FEATURE:
<221> NAME/KEY: MISC_FEATURE
<223> OTHER INFORMATION: fusion protein

<400> SEQUENCE: 1

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95
```

-continued

```
Lys Pro Met Asp Ile Asp Pro Tyr Lys Glu Phe Gly Ala Thr Val Glu
            100                 105                 110

Leu Leu Ser Phe Leu Pro Ser Asp Phe Pro Ser Val Arg Asp Leu
        115                 120                 125

Leu Asp Thr Ala Ser Ala Leu Tyr Arg Glu Ala Leu Glu Ser Pro Glu
        130                 135                 140

His Cys Ser Pro His His Thr Ala Leu Arg Gln Ala Ile Leu Cys Trp
145                 150                 155                 160

Gly Glu Leu Met Thr Leu Ala Thr Trp Val Gly Asn Asn Leu Glu Asp
                165                 170                 175

Pro Ala Ser Arg Asp Leu Val Val Asn Tyr Val Asn Thr Asn Met Gly
            180                 185                 190

Leu Lys Ile Arg Gln Leu Leu Trp Phe His Ile Ser Cys Leu Thr Phe
        195                 200                 205

Gly Arg Glu Thr Val Leu Glu Tyr Leu Val Ser Phe Gly Val Trp Ile
        210                 215                 220

Arg Thr Pro Pro Ala Tyr Arg Pro Pro Asn Ala Pro Ile Leu Ser Thr
225                 230                 235                 240

Leu Pro Glu Thr Thr Val Val Arg Arg Asp Arg Gly Arg Ser Pro
                245                 250                 255

Arg Arg Arg Thr Pro Ser Pro Arg Arg Arg Ser Gln Ser Pro Arg
            260                 265                 270

Arg Arg Arg Ser Gln Ser Arg Glu Ser Gln Cys Met Ala Lys Thr Ile
        275                 280                 285

Ala Tyr Asp Glu Glu Ala Arg Arg Gly Leu Glu Arg Gly Leu Asn Ala
        290                 295                 300

Leu Ala Asp Ala Val Lys Val Thr Leu Gly Pro Lys Gly Arg Asn Val
305                 310                 315                 320

Val Leu Glu Lys Lys Trp Gly Ala Pro Thr Ile Thr Asn Asp Gly Val
                325                 330                 335

Ser Ile Ala Lys Glu Ile Glu Leu Glu Asp Pro Tyr Glu Lys Ile Gly
            340                 345                 350

Ala Glu Leu Val Lys Glu Val Ala Lys Lys Thr Asp Asp Val Ala Gly
        355                 360                 365

Asp Gly Thr Thr Thr Ala Thr Val Leu Ala Gln Ala Leu Val Arg Glu
        370                 375                 380

Gly Leu Arg Asn Val Ala Ala Gly Ala Asn Pro Leu Gly Leu Lys Arg
385                 390                 395                 400

Gly Ile Glu Lys Ala Val Glu Lys Val Thr Glu Thr Leu Leu Lys Gly
                405                 410                 415

Ala Lys Glu Val Glu Thr Lys Glu Gln Ile Ala Ala Thr Ala Ala Ile
            420                 425                 430

Ser Ala Gly Asp Gln Ser Ile Gly Asp Leu Ile Ala Glu Ala Met Asp
        435                 440                 445

Lys Val Gly Asn Glu Gly Val Ile Thr Val Glu Glu Ser Asn Thr Phe
        450                 455                 460

Gly Leu Gln Leu Glu Leu Thr Glu Gly Met Arg Phe Asp Lys Gly Tyr
465                 470                 475                 480

Ile Ser Gly Tyr Phe Val Thr Asp Pro Glu Arg Gln Glu Ala Val Leu
                485                 490                 495

Glu Asp Pro Tyr Ile Leu Leu Val Ser Ser Lys Val Ser Thr Val Lys
            500                 505                 510

Asp Leu Leu Pro Leu Leu Glu Lys Val Ile Gly Ala Gly Lys Pro Leu
        515                 520                 525
```

```
Leu Ile Ile Ala Glu Asp Val Glu Gly Glu Ala Leu Ser Thr Leu Val
        530                 535                 540

Val Asn Lys Ile Arg Gly Thr Phe Lys Ser Val Ala Val Lys Ala Pro
545                 550                 555                 560

Gly Phe Gly Asp Arg Arg Lys Ala Met Leu Gln Asp Met Ala Ile Leu
                565                 570                 575

Thr Gly Gly Gln Val Ile Ser Glu Glu Val Gly Leu Thr Leu Glu Asn
            580                 585                 590

Ala Asp Leu Ser Leu Leu Gly Lys Ala Arg Lys Val Val Thr Lys
            595                 600                 605

Asp Glu Thr Thr Ile Val Glu Gly Ala Gly Asp Thr Asp Ala Ile Ala
610                 615                 620

Gly Arg Val Ala Gln Ile Arg Gln Glu Ile Glu Asn Ser Asp Ser Asp
625                 630                 635                 640

Tyr Asp Arg Glu Lys Leu Gln Glu Arg Leu Ala Lys Leu Ala Gly Gly
                645                 650                 655

Val Ala Val Ile Lys Ala Gly Ala Ala Thr Glu Val Glu Leu Lys Glu
            660                 665                 670

Arg Lys His Arg Ile Glu Asp Ala Val Arg Asn Ala Lys Ala Ala Val
            675                 680                 685

Glu Glu Gly Ile Val Ala Gly Gly Val Thr Leu Leu Gln Ala Ala
690                 695                 700

Pro Thr Leu Asp Glu Leu Lys Leu Glu Gly Asp Glu Ala Thr Gly Ala
705                 710                 715                 720

Asn Ile Val Lys Val Ala Leu Glu Ala Pro Leu Lys Gln Ile Ala Phe
                725                 730                 735

Asn Ser Gly Leu Glu Pro Gly Val Val Ala Glu Lys Val Arg Asn Leu
            740                 745                 750

Pro Ala Gly His Gly Leu Asn Ala Gln Thr Gly Val Tyr Glu Asp Leu
            755                 760                 765

Leu Ala Ala Gly Val Ala Asp Pro Val Lys Val Thr Arg Ser Ala Leu
770                 775                 780

Gln Asn Ala Ala Ser Ile Ala Gly Leu Phe Leu Thr Thr Glu Ala Val
785                 790                 795                 800

Val Ala Asp Lys Pro Glu Lys Glu Lys Ala Ser Val Pro Gly Gly Gly
                805                 810                 815

Asp Met Gly Gly Met Asp Phe
                820

<210> SEQ ID NO 2
<211> LENGTH: 2476
<212> TYPE: DNA
<213> ORGANISM: artificial sequence
<220> FEATURE:
<221> NAME/KEY: misc_feature
<223> OTHER INFORMATION: fusion protein

<400> SEQUENCE: 2
atgcatggag atacacctac attgcatgaa tatatgttag atttgcaacc agagacaact      60
gatctctact gttatgagca attaaatgac agctcagagg aggaggatga aatagatggt     120
ccagctggac aagcagaacc ggacagagcc cattacaata ttgtaacctt ttgttgcaag     180
tgtgactcta cgcttcggtt gtgcgtacaa agcacacacg tagacattcg tactttggaa     240
gacctgttaa tgggcacact aggaattgtg tgccccatct gttctcagaa accaatggac     300
attgaccctt ataagaatt tggagctact gtggagttac tctcgttttt gccttctgac     360
```

```
ttctttcctt ccgtcagaga tctcctagac accgcctcag ctctgtatcg ggaagcctta    420
gagtctcctg agcattgctc acctcaccat actgcactca ggcaagccat tctctgctgg    480
ggggaattga tgactctagc tacctgggtg gtaataatt tggaagatcc agcatccagg     540
gatctagtag tcaattatgt taatactaac atgggtttaa agatcaggca actattgtgg    600
tttcacatat cttgccttac ttttggaaga gagactgtac ttgaatattt ggtatctttc    660
ggagtgtgga ttcgcactcc tccagcctat agaccaccaa atgcccctat cttatcaaca    720
cttccggaaa ctactgttgt tagacgacgg gaccgaggcg ggtccctag aagaagaact     780 ccctcgcctc gcagacgcag atctcaatcg ccgcgtcgca gaagatctca atctcgggaa    840
tctcaatgta tggccaagac aattgcgtac gacgaagagg cccgtcgcgg cctcgagcgg    900
ggcttgaacg ccctcgccga tgcggtaaag gtgacattgg ccccaaggg ccgcaacgtc     960 gtcctggaaa agaagtgggg tgccccacg atcaccaacg atggtgtgtc catcgccaag    1020
gagatcgagc tggaggatcc gtacgagaag atcggcgccg agctggtcaa agaggtagcc   1080
aagaagaccg atgacgtcgc cggtgacggc accacgacgg ccaccgtgct ggcccaggcg   1140
ttggttcgcg agggcctgcg caacgtcgcg gccggcgcca acccgctcgg tctcaaacgc   1200
ggcatcgaaa aggccgtgga aaggtcacc gagaccctgc tcaagggcgc caaggaggtc    1260
gagaccaagg agcagattgc ggccaccgca gcgatttcgg cgggtgacca gtccatcggt   1320
gacctgatcg ccgaggcgat ggacaaggtg gcaacgagg cgtcatcac cgtcgaggag     1380 tccaacacct ttgggctgca gctcgagctc accgagggta tgcggttcga caagggctac   1440
atctcggggt acttcgtgac cgacccggag cgtcaggagg cggtcctgga ggaccctac    1500 atcctgctgg tcagctccaa ggtgtccact gtcaaggatc tgctgccgct gctcgagaag   1560
gtcatcggag ccggtaagcc gctgctgatc atcgccgagg acgtcgaggg cgaggcgctg   1620
tccaccctgg tcgtcaacaa gatccgcggc accttcaagt cggtggcggt caaggctccc   1680
ggcttcggcg accgccgcaa ggcgatgctg caggatatgg ccattctcac cggtggtcag   1740
gtgatcagcg aagaggtcgg cctgacgctg gagaacgccg acctgtcgct gctaggcaag   1800
gcccgcaagg tcgtggtcac caaggacgag accaccatcg tcgagggcgc cggtgacacc   1860
gacgccatcg ccggacgagt ggcccagatc cgccaggaga tcgagaacag cgactccgac   1920
tacgaccgtg agaagctgca ggagcggctg gccaagctgg ccggtggtgt cgcggtgatc   1980
aaggccggtg ccgccaccga ggtcgaactc aaggagcgca agcaccgcat cgaggatgcg   2040
gttcgcaatg ccaaggccgc cgtcgaggag ggcatcgtcg ccggtggggg tgtgacgctg   2100
ttgcaagcgg ccccgacccct ggacgagctg aagctcgaag gcgacgaggc gaccggcgcc   2160
aacatcgtga aggtggcgct ggaggccccg ctgaagcaga tcgccttcaa ctccgggctg   2220
gagccgggcg tggtggccga aaggtgcgc aacctgccgg ctggccacgg actgaacgct    2280
cagaccggtg tctacgagga tctgctcgct gccggcgttg ctgacccggt caaggtgacc   2340
cgttcggcgc tgcagaatgc ggcgtccatc gcggggctgt tcctgaccac cgaggccgtc   2400
gttgccgaca agccggaaaa ggagaaggct tccgttcccg gtggcggcga catgggtggc   2460
atggatttct gaattc                                                    2476
```

MATERIAL WITH IMMUNOGENICITY

This application is a national phase of International Application No. PCT/CN2008/071346 filed on Jun. 18, 2008 and published in the Chinese language, which claims priority to U.S. Provisional Patent Application Ser. No. 60/944,780 filed on Jun. 18, 2007 and U.S. Provisional Patent Application Ser. No. 60/951,856 filed on Jul. 25, 2007.

TECHNICAL FIELD

The present invention relates to a fusion protein comprising a human papillomavirus E7 antigen, a viral capsid protein and a molecular chaperone protein, an immunogenic macromolecule polymerized from said fusion protein, and uses thereof.

BACKGROUND OF THE INVENTION

The human papillomavirus (HPV) is a small, uncoated, double-stranded DNA virus that infects through the surface of skin and mucosa and is implicated to a variety of diseases. Skin HPV infection may cause verrucae on the hand or foot that can persist for months to years. Such a benign pathological change is generally not life-threatening except for rare cases, but may cause pain to the patient. Mucosal HPV infects the regions of the anus and the genital as well as the oral cavity. Nearly 100 different types of HPV have been identified up to date. Almost 40 subtypes of HPV specifically infect the genital system and the mucous membranes of the oral cavity. These types of HPV will not induce any symptoms upon infection and rarely give rise to visible genital verrucae, while the symptoms typically are gradually manifested after 2-3 months with viral infection. Infection may not be known until 3 weeks to several years later, therefore HPV spreads unknowingly. Most of the occurrences of infection is asymptomatic, but may lead to genital verrucae and cancers of the anus and the genital tract. The genital verrucae resulting from mucosal HPV infection is considered as one of a number of sexually transmitted diseases (STD), and its occurrence worldwide being two times that of herpes simplex virus infection. Persistent HPV infection may lead to a premalignant lesion—cervical intraepithelial neoplasia (CIN), some cases of which may develop into cervical cancer. Cervical cancer has a very high occurrence in the world, most cases of which are detected positive for HPV 16 and HPV18 DNA (>99%). Cervical cancer has a morbidity of 9.98 in 100 thousand people, resulting in an increase of 500,000 patients throughout the world each year, and is the most significant causative factor of death of women under the age of 50. Besides cervical cancer, HPV is also implicated in many anal and perianal cancers.

The preventive vaccine has been developed at present. Major capsid protein for HPV has been expressed in eukaryotic cells and it can form virus-like particles (VLPs) in the expression host. Purified VLPs are useful as effective preventive vaccine against HPV infection. However, there are no available effective therapeutic compositions yet for curing such infection. Since the virus makes use of many of the host's own mechanisms for its replication, it is difficult to develop a drug that inhibits viral replication without harming the host. It is known that the immune system plays an important role in controlling HPV infection. The fact of increase in the possibility of HPV infection among people having received immunosuppressive treatment also demonstrates the control over viral infection by the immune system. The researches on the abatement of naturally-occurring verrucae also show evidences of the ability of the immune system to curb infection. The natural abatement of some external genitalia verrucae would happen in some subjects. Histological studies have shown the occurrence of a significant numbers of T lymphocytes in the afflicted area, leading to the assumption that the effective immune response against HPV infection is mainly mediated by cellular immunity. Moreover, natural abatement of verrucae is associated with lymphocyte infiltration, titillation, rubefacientness in the infection area and other symptoms relevant to cell-mediated immune responses. HPV infection followed by induction of lesions is commonly seen in patients with impaired cell-mediated immunity. Therefore, the induction of effective cell-mediated immune responses against HPV antigens is key to the development of vaccine against HPV infection.

The studies on preventive vaccine focus on L1 protein. This protein can effectively activate organisms to generate strong and persistent humoral immunity, allowing for the efficacious prevention of certain subtypes of HPV infection, but it is not effective for the treatment of lesions following HPV infection. E6 and E7, two HPV proteins that can induce and maintain cell transformation, are expressed in the HPV-infected tumor cells and are ideal therapeutic targets. Therefore, therapeutic compositions directed to E6 and E7 provide options for controlling the diseases associated with HPV infection. By using suitable antigen presenting systems (or antigen carriers), E6 and E7 or determinants thereof can be presented to the host to induce strong, long-lasting and specific cell-mediated immune responses, which may cure the diseases associated with HPV infection.

The HPV L1 and L2 capsid protein has been used as the carrier system for transporting HPV E6 or E 7 protein antigens to induce cell-mediated immune responses. Immune tolerance to HPV may be induced in the host due to certain immunity to HPV that the infected host possesses, or due to the latency or persistent infection of HPV in the infected host. In fact, although HPV capsid protein has potential immunogenicity, only half of the patients with cervical cancer can generate immunoglobin G (IgG) specific for the capsid protein. Such a pre-existing immunity or immune tolerance caused by HPV L1 or L2 capsid protein may restrict the efficacy of therapeutic vaccine.

When recombinantly expressed in a suitable expression system, capsid proteins derived from other viruses are also capable of self-assembly into VLPs in a suitable host. These VLPs can also be used as the antigen presenting systems (or antigen carriers) for presenting E6 or E7 antigens or determinants thereof to induce cell-mediated immune responses. However, the purification of the VLPs is still a concern. If VLPs are derived from viruses whose host is human, the resulting therapeutic vaccine also faces the problem of immune tolerance.

Accordingly, there is a need in the art to provide a therapeutic composition for treating the diseases associated with HPV infection.

SUMMARY OF THE INVENTION

It is an object of the present invention to provide a fusion protein comprising a human papillomavirus E7 antigen, a viral capsid protein and a molecular chaperone protein.

It is another object of the present invention to provide an immunogenic macromolecule mainly polymerized from the fusion protein according to the present invention by self-assembly of the fusion protein.

It is yet another object of the present invention to provide a composition (such as vaccine) comprising said immunogenic macromolecule.

In the first aspect of the present invention provided is a fusion protein comprising a human papillomavirus E7 antigen, a viral capsid protein and a molecular chaperone protein.

In another preferred embodiment, said human papillomavirus E7 antigen is a full-length human papillomavirus E7 antigen or a protein fragment containing the antigenic determinant thereof.

In another preferred embodiment, said human papillomavirus E7 antigen, said viral capsid protein and said molecular chaperone protein are linked through chemical bonds or are coupled with one another; said chemical bonds are covalent bonds or non-covalent bonds.

In another preferred embodiment, said chemical bonds are peptide bonds.

In another preferred embodiment, said fusion protein comprises in turn, from the amino terminal to the carboxylterminal, human papillomavirus E7 antigen, viral capsid protein and molecular chaperone protein.

In another preferred embodiment, a linking peptide (such as 2-20 aa, preferably 2-10 aa) is comprised between said viral capsid protein and said molecular chaperone protein, wherein said linking peptide having at least one restriction enzyme cutting site.

In another preferred embodiment, said restriction enzyme cutting site is selected from (but not limited to) enterokinase cutting site, thrombin cutting site or trypsin cutting site.

In another preferred embodiment, said viral capsid protein is hepatitis B virus core antigen.

In another preferred embodiment, said viral capsid protein is a full-length viral capsid protein, or a fragment that retains the ability of self-assembly thereof, or a variant that retains the ability of self-assembly thereof.

In another preferred embodiment, said molecular chaperone protein is selected from one member of the molecular chaperone protein family.

In another preferred embodiment, said molecular chaperone protein is a full-length molecular chaperone protein, or a fragment that retains the biological activity thereof, or a variant that retains the biological activity thereof.

In another preferred embodiment, said molecular chaperone protein is selected from: heat shock protein 65 (Hsp65), heat shock protein 60 (Hsp60), heat shock protein 70 (Hsp70), heat shock protein 90 (Hsp90) or heat shock protein 100 (Hsp100).

In another preferred embodiment, said molecular chaperone protein is heat shock protein 65.

In another preferred embodiment, said molecular chaperone protein is *M. bovis* BCG Hsp65.

In another preferred embodiment, said human papillomavirus E7 antigen is: (a1) a protein having the sequence of amino acids from position 1 to 98 depicted in SEQ ID NO: 1, or a protein derived from (a1) having the same immunogenicity as the protein defined in (a1), formed by substitution, deletion or addition of one or more amino acid residues in the amino acid sequence defined in (a1); or said viral capsid protein is: (b1) a protein having the sequence of amino acids from position 99 to 283 depicted in SEQ ID NO: 1, or a protein derived from (b1) having the same function as the protein defined in (b1), formed by substitution, deletion or addition of one or more amino acid residues in the amino acid sequence defined in (b1); or said molecular chaperone protein is: (c1) a protein having the sequence of amino acids from position 284 to 823 depicted in SEQ ID NO: 1, or a protein derived from (c1) having the same function as the protein defined in (c1), formed by substitution, deletion or addition of one or more amino acid residues in the amino acid sequence defined in (c1).

In the second aspect of the present invention provided is the use of said fusion protein in the manufacture of an immunogenic macromolecule.

In the third aspect of the present invention provided is a nucleic acid molecule that encodes said fusion protein.

In the fourth aspect of the present invention provided is a vector comprising said nucleic acid.

In the fifth aspect of the present invention provided are cells comprising said vector or having said nucleic acid molecule integrated into their genome.

In the sixth aspect of the present invention provided is an immunogenic macromolecule that is a multi-molecule polymer mainly formed from said fusion protein through self-assembly of said fusion protein and having a molecular weight of more than 1,000 KD.

In another preferred embodiment, said immunogenic macromolecule is a particulate multi-molecule polymer having a different morphology from that of the virus-like particles.

In another preferred embodiment, said immunogenic macromolecule has a particle diameter of 1-1,000 nm.

In another preferred embodiment, said macromolecule further comprises at least one immunostimulant for enhancing the immune responses of the organisms.

In another preferred embodiment, said immunostimulant is coupled with said immunogenic macromolecule or is packed into said immunogenic macromolecule; said immunostimulant being selected from: double-stranded RNA or non-methylated CpG-DNA.

In the seventh aspect of the present invention provided is a method for preparing said immunogenic macromolecule, said method comprising:

(1) culturing said cell to express said fusion protein;

(2) separating and purifying the fusion protein obtained from (1), wherein a chaotropic agent is used in one or more steps in the separation and purification process; and (3) allowing the fusion protein obtained from (2) to self-assemble to form said immunogenic macromolecule by removing the chaotropic agent.

In another preferred embodiment, said chaotropic agent is selected from urea or guanidine hydrochloride.

In another preferred embodiment, said urea has a concentration in the range of 1-10 M, preferably in the range of 2-8 M, more preferably in the range of 4-8 M.

In another preferred embodiment, said guanidine hydrochloride has a concentration in the range of 1-10 M, preferably in the range of 1-6 M, more preferably in the range of 3-6 M.

In the eighth aspect of the present invention provided is the use of said macromolecule in the manufacture of a composition for the prevention or treatment of the diseases associated with human papillomavirus (HPV) infection.

In another preferred embodiment, said diseases are selected from (but not limited to): tumors (such as cervical cancer, vaginal cancer, anal and perianal cancers, oropharyngeal cancer, maxillary sinus cancer, lung cancer), cervical intraepithelial neoplasia and external genital verrucae.

In another preferred embodiment, said immunogenic macromolecule as an antigen carrier or vaccine can escape from the immune response or immune tolerance to virus-like particles which is present in the organisms.

In the ninth aspect of the present invention provided is an immunogenic composition comprising (a) said immunogenic macromolecule; and (b) a pharmaceutically acceptable carrier.

In the tenth aspect of the present invention provided is the use of said immunogenic composition in the prevention or treatment of the diseases associated with HPV infection.

In the eleventh aspect of the present invention provided is a method of preventing or treating the diseases associated with HPV infection, said method comprising administering to the subject in need thereof an effective amount of said immunogenic macromolecule or said immunogenic composition.

BRIEF DESCRIPTION OF THE DRAWINGS

FIG. 5 is the electron microscope photoes of the multi-molecule polymer according to the present invention.

DETAILED DESCRIPTION OF THE PRESENT INVENTION

Figure 1:
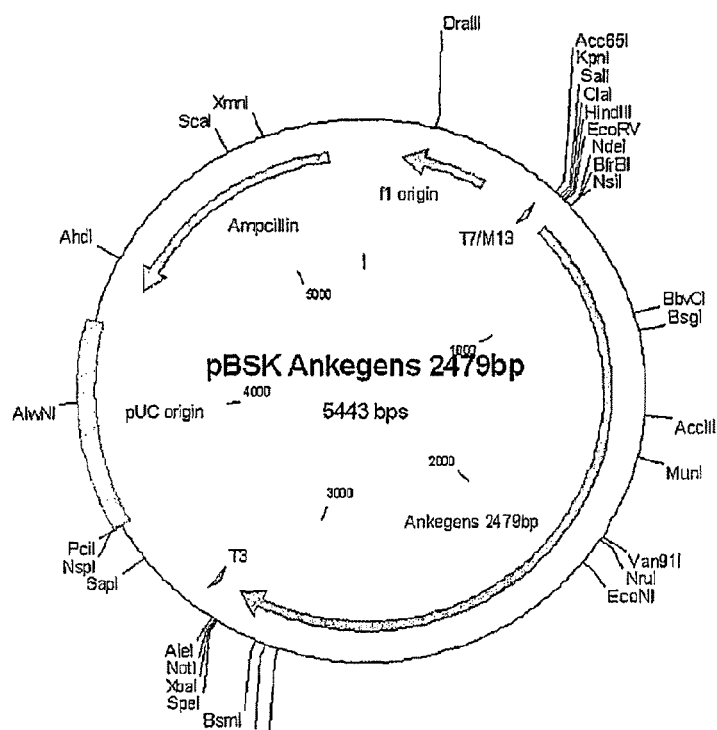
FIG. 1 shows the construction of the recombinant plasmid in Example 1 of the present invention.

Through intensive studies, the present inventor discloses for the first time a fusion protein comprising a human papillomavirus E7 antigen, a viral capsid protein and a molecular chaperone protein. After expression followed by purification under denaturing conditions (such as by using a high concentration of chaotropic agent), said fusion protein can undergo renaturation and self-assembly in soluble form to constitute a macromolecule with high immunogenicity. Said macromolecule is a particulate multi-molecule polymer having a different morphology from that of the virus-like particles and can circumvent the immune response or immune tolerance to virus-like particles which is present in the organisms.

As used herein, the terms "fusion protein according to the present invention", "a fusion protein comprising a human papillomavirus E7 antigen, a viral capsid protein and a molecular chaperone protein" and "E7-Core-Hsp65 fusion protein" are used interchangeably to refer to a protein formed by fusion of a human papillomavirus E7 antigen, a viral capsid protein and a molecular chaperone protein, wherein said human papillomavirus E7 antigen, said viral capsid protein and said molecular chaperone protein may be linked through chemical bonds or coupled with one another. Preferably, they are linked through chemical bonds (such as peptide bonds) with or without linking peptide sequence(s).

As used herein, the term "immunogenic macromolecule" refers to a macromolecule comprising a number of monomeric fusion proteins. Preferably, it is polymerized or assembled from a number of monomeric fusion proteins. Said immunogenic macromolecule is particulate, having a different morphology from that of the virus-like particles.

As used herein, the phrases "comprising", "having" or "including" (or grammatical variants thereof) encompass "containing", "substantially consisting of . . . ", "essentially consisting of . . . " and "consisting of . . . ". "Substantially consisting of . . . ", "essentially consisting of . . . " and "consisting of . . . " are subordinate concepts of "comprising", "having" or "including".

Fusion Protein

The present invention provides a fusion protein comprising a human papillomavirus E7 antigen, a viral capsid protein and a molecular chaperone protein, which is useful to form an immunogenic macromolecule. Preferably, said fusion protein is an isolated protein free of association with other proteins, peptides or molecules, and is a pure product or a purified extract from the culture of recombinant host cells.

1. Human Papillomavirus E7 Antigen

Human papillomavirus E7 antigen or a biologically active fragment thereof (such as a protein fragment containing the antigenic determinant thereof) can be used in the present invention. By a biologically active fragment of human papillomavirus E7 antigen is meant a polypeptide fragment that retains all or part of the immunogenicity of the full-length human papillomavirus E7 antigen after it is linked with a viral capsid protein and a molecular chaperone protein (preferably linked with a viral capsid protein, more preferably linked to the N-terminal of a viral capsid protein) to form a fusion protein. Normally, said biologically active fragment retains at least 50% of the immunogenicity of the full-length human papillomavirus E7 antigen. More preferably, said biologically active fragment retains 60%, 70%, 80%, 90%, 95%, 99% or 100% of the immunogenicity of the full-length human papillomavirus E7 antigen.

Human papillomavirus E7 antigen or a biologically active fragment thereof comprises a part of sequence having conservative amino acid substitutions therein which basically has no effect on said immunogenicity. It is a well-known and easy-to-perform technology in the art to make appropriate amino acid substitutions without change of biological activity of the resulting molecule. Generally, a single amino acid change in the non-essential regions of a polypeptide will basically not alter the biological activity. See Watson et. al., Molecular Biology of The Gene, the $4^{th}$ edition, 1987, The Benjamin/Cummings Pub. Co., P224. Examples of such substitutions are shown in Table 1.

TABLE 1

| Original amino acid residues | Conservative substitutions |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; phe |
| Val (V) | Ile; Leu |

Other similar substitutions may exist that can be determined empirically or based on known conservative sequences.

In preferred embodiments of the present invention, the amino acid sequence for said human papillomavirus E7 antigen can be essentially identical to the sequence from position 1 to 98 depicted in SEQ ID NO: 1, and the encoding sequence for said human papillomavirus E7 antigen can be essentially identical to the sequence from position 1 to 294 depicted in SEQ ID NO: 2.

2. Viral Capsid Protein

The viral capsid protein according to the present invention can be any suitable capsid protein derived from viruses so long as it is capable of self-assembly and retains the ability of self-assembly after it is linked with said human papillomavirus E7 antigen and said molecular chaperone protein to form the fusion protein according to the present invention.

Said viral capsid protein is a full-length viral capsid protein, or a biologically active fragment thereof that retains the ability of self-assembly, or a variant thereof that retains the ability of self-assembly.

By a biologically active fragment of viral capsid protein is meant a polypeptide fragment that retains all or part of the ability of self-assembly of the full-length viral capsid protein. Normally, said biologically active fragment retains at least 50% of the ability of self-assembly of the full-length viral capsid protein. More preferably, said biologically active fragment retains 60%, 70%, 80%, 90%, 95%, 99% or 100% of the ability of self-assembly of the full-length viral capsid protein.

Full-length viral capsid protein or a biologically active fragment thereof comprises a part of sequence having conservative amino acid substitutions therein which basically has no effect on said ability of self-assembly. Examples of such substitutions are shown in Table 1. Other similar substitutions may exist that can be determined empirically or based on known conservative sequences.

In preferred embodiments of the present invention, said viral capsid protein is hepatitis B virus (HBV) core antigen. In a particular embodiment of the present invention, said viral capsid protein is of hepatitis B virus ADW2 subtype.

Methods for producing the biologically active fragment or variant of said capsid protein are available in published literature (Koschel M, Thomssen R, Bruss V. 1999. Extensive mutagenesis of the hepatitis B virus core gene and mapping of mutations that allow capsid formation. J Virol. 73(3):2153-60; Paintsil J, Muller M, Picken M, Gissmann L, Zhou J. 1996. Carboxyl terminus of bovine papillomavirus type-1 L1 protein is not required for capsid formation. Virology. 223(1): 238-44; Beames B, Lanford R E. 1995. Insertions within the hepatitis B virus capsid protein influence capsid formation and RNA encapsidation. J Virol. 69(11):6833-8).

In preferred embodiments of the present invention, the amino acid sequence for said viral capsid protein can be essentially identical to the sequence from position 99 to 283 depicted in SEQ ID NO: 1, and the encoding sequence for said viral capsid protein can be essentially identical to the sequence from position 295 to 849 depicted in SEQ ID NO: 2.

3. Molecular Chaperone Protein

The molecular chaperone protein according to the present invention can be any suitable protein from the molecular chaperone protein family so long as it can bind with proteins of non-natural configuration or denatured proteins to prevent the formation of denatured aggregates and facilitate the proper renaturation of the aggregates, so that the denatured fusion protein can undergo renaturation and self-assembly.

Said molecular chaperone protein is a full-length molecular chaperone protein, or a biologically active fragment that retains its biological function thereof, or a variant that retains its biological function thereof.

By a biologically active fragment of molecular chaperone protein is meant a polypeptide fragment that retains all or part of the biological function of the full-length molecular chaperone protein. Normally, said biologically active fragment retains at least 50% of the biological function of m the full-length molecular chaperone protein. More preferably, said biologically active fragment retains 60%, 70%, 80%, 90%, 95%, 99% or 100% of the biological function of the full-length molecular chaperone protein.

Full-length molecular chaperone protein or a biologically active fragment thereof comprises a part of sequence having conservative amino acid substitutions therein which basically has no effect on said biological function. Examples of such substitutions are shown in Table 1. Other similar substitutions may exist that can be determined empirically or based on known conservative sequences.

Methods for producing the biologically active fragment or variant of said molecular chaperone protein are available in published literature (Jewett A I, Shea J E. 2006. Folding on the chaperone: yield enhancement through loose binding. J Mol. Biol. 363(5):945-57; Bhattacharyya J, Padmanabha Udupa E G, Wang J, Sharma K K. 2006. Mini-alphaB-crystallin: a functional element of alphaB-crystallin with chaperone-like activity. Biochemistry. 45(9):3069-76; Ramon-Luing L A, Cruz-Migoni A, Ruiz-Medrano R, Xoconostle-Cazarea B, Ortega-Lopez J. 2006. One-step purification and immobilization in cellulose of the GroEL apical domain fused to a carbohydate-binding module and its use in protein refolding. Biotechnol Lett. 28(5):301-7; Fox J D, Routzahn K M, Bucher M H, Waugh D S. 2003. Maltodextrin-binding proteins from diverse bacteria and archaea are potent solubility enhancers. FEBS Lett. 537(1-3):53-7; Fox J D, Kapust R B, Waugh D S, 2001. Single amino acid substitutions on the surface of *Escherichia coli* maltose-binding protein can have a profound impact on the solubility of fusion proteins. Protein Sci. 10(3):622-30; Chatellier J, Buckle A M, Fersht A R. 1999. GroEL recognises sequential and non-sequential linear structural motifs compatible with extended beta-strands and alpha-helices. J Mol. Biol. 292(1):163-72). In bacteria such as *E. Coli*, molecular chaperone proteins tend to have a very high level of expression under adverse conditions, such as high temperature. Therefore, this type of molecular chaperone proteins is traditionally also referred to heat shock proteins (Hsps). The expression of molecular chaperone proteins is usually associated with induction by heat or other conditions adverse to the cell, because the proper folding process of proteins is significantly affected at a relatively high temperature such that molecular chaperone proteins are required to repair the damage to cells possibly caused by the misfolding of some of the proteins. Common molecular chaperone protein families include Hsp 60, Hsp70, Hsp90, Hsp100 and small molecular weight Hsp proteins. Molecular chaperone proteins are not limited to heat shock proteins. Other molecular chaperone proteins also can, using the method according to the present invention, be fused with viral capsid proteins to construct fusion proteins for preparing the immunogenic macromolecule according to the present invention.

In preferred embodiments of the present invention, said molecular chaperone protein is *M. Bovis* BCG hsp65.

In preferred embodiments of the present invention, the amino acid sequence for said molecular chaperone protein can be essentially identical to the sequence from position 284 to 823 in SEQ ID NO: 1, and the encoding sequence for said molecular chaperone protein can be essentially identical to the sequence from position 850 to 2469 in SEQ ID NO: 2.

4. Linkage

Said human papillomavirus E7 antigen, said viral capsid protein and said molecular chaperone protein are linked through chemical bonds or are coupled with one another; said chemical bonds being covalent bonds or non-covalent bonds.

In preferred embodiments of the present invention, said human papillomavirus E7 antigen, said viral capsid protein and said molecular chaperone protein are linked through chemical bonds, said chemical bonds preferably being peptide bonds.

Alternatively, said viral capsid protein and said molecular chaperone protein are linked through a chemical bond, while said human papillomavirus E7 antigen and said viral capsid protein are coupled with each other.

In preferred embodiments of the present invention, said fusion protein comprises, from the amino terminal to the carboxyl terminal, human papillomavirus E7 antigen, viral capsid protein and molecular chaperone protein.

Said human papillomavirus E7 antigen, said viral capsid protein and said molecular chaperone protein can be linked to one another directly, or they can be linked through polypeptide linkers (linking peptides). The linkers, which each for example comprise 1-50 amino acids, preferably 1-30 amino acids, are disposed in a manner such that they basically have no effect on the self-assembly of the fusion protein to form immunogenic macromolecules.

In preferred embodiments of the present invention, a linking peptide (such as 2-20 aa, preferably 2-10 aa) is comprised between said viral capsid protein and said molecular chaperone protein. Said linking peptide has at least one restriction enzyme cutting site, which is selected from (but not limited to) enterokinase cutting site, thrombin cutting site or trypsin cutting site. The restriction enzyme cutting site is disposed in a manner that facilitates the subsequent cleavage of said molecular chaperone protein from said fusion protein or said macromolecule particle. The fusion protein thus designed and constructed is subjected to recombinant expression, separation and purification, renaturation, and self-assembly to form an immunogenic macromolecule (multi-molecule polymer), from which the molecular chaperone protein can be cleaved using a specific enzyme to obtain the final macromolecule containing only the capsid protein. For example, the sequence of Asp-Asp-Asp-Asp-Lys can be specifically recognized by enterokinase. When introducing such sequence into the binding site of the fusion protein according to the present invention, the molecular chaperone protein may be cleaved from the macromolecule formed by said fusion protein with enterokinase to obtain, after separation and purification, the macromolecule containing only the capsid protein.

5. Nucleic Acid Molecule

In another aspect, the present invention provides an isolated nucleic acid that encodes said fusion protein or a complementary strand thereof. Any nucleic acid that encodes said fusion protein is useful for the present invention. The sequences mentioned in the following Examples are all suitable for the method according to the present invention.

The DNA sequence encoding the fusion protein according to the present invention can be artificially synthesized in full length. Alternatively, DNA sequences respectively encoding said human papillomavirus E7 antigen, said viral capsid protein and said molecular chaperone protein can be obtained by PCR amplification and then link together to form the DNA sequence encoding the fusion protein according to the present invention.

6. Expression Vector

The present invention also provides a vector comprising the nucleic acid molecule that encodes said fusion protein. Said vector may further comprise an expression regulation sequence operably linked to the sequence of said nucleic acid molecule for facilitating the expression of said fusion protein.

As used herein, "operably linked to" refers to a condition where certain portions of a linear DNA sequence may affect the activities of other portions of the same linear DNA sequence. For example, if a promoter controls the transcription of an encoding sequence, it is operably linked to the encoding sequence.

Any suitable vector can be used in the present invention, such as some of the vectors used in the cloning and expression of bacterial, fungal, yeast and mammal cells, as described in Pouwels et. al., Cloning Vectors: A Laboratory Manual.

7. Host Cells

The recombinant cells comprising the nucleic acid sequence that encodes said fusion protein are also included in the present invention.

As used herein, the term "host cells" includes both prokaryotic and eukaryotic cells. Prokaryotic host cells commonly used include *E. coli, Bacillus subtilis*, etc, such as *E. coli* HMS174(DE3), or BL21(DE3). Eukaryotic host cells commonly used include yeast cells, insect cells and mammal cells. In preferred embodiments of the present invention, prokaryotic cells are used as the host cells.

8. Method for Producing the Fusion Protein

The method for producing the fusion protein is also included in the present invention. Said method comprises culturing the recombinant cells comprising the nucleic acid that encodes the fusion protein. Said method may include allowing the cell to express the encoded fusion protein and allowing the expressed fusion protein to undergo renaturation. Said method may further include separating and/or purifying the renatured fusion protein.

The fusion protein obtained as described above can be purified to the protein with essential homogeneity, such as exhibiting a single band in SDS-PAGE electrophoregram.

9. Use of the Fusion Protein

The fusion protein according to the present invention can be used to prepare an immunogenic macromolecule for inducing immune responses in the organisms, including cell-mediated immune responses.

Immunogenic Macromolecule and Method of Preparation Thereof

The present invention further provides an immunogenic macromolecule which is a multi-molecule polymer. Said polymer comprises said fusion protein, and preferably, said polymer is essentially polymerized from said fusion protein. Said immunogenic macromolecule is a particulate multi-molecule polymer having a different morphology from that of the virus-like particles. Said immunogenic macromolecule typically has a particle diameter of about 1-1000 nm, preferably about 5-500 nm, more preferably about 10-100 nm, such as about 20 nm, 40 nm, 60 nm or 80 nm.

The organism's MHC class I and class II immune systems present exogenous antigens which are in particulate form 1,000 or 10,000 times more than they do soluble monomeric antigens. That is, antigens in particulate form are much more immunogenic than soluble monomeric antigens.

Individual denatured capsid protein molecules tend to form amorphous aggregate particles and fail to form virus-like particles during renaturation. Moreover, individual denatured capsid protein molecules generally cannot be present in soluble form in solutions without a chaotropic agent due to the formation of aggregate particles. It may be related to the interactions among the hydrophobic groups in the capsid protein molecules. These hydrophobic groups play a critical role in the self-assembly of capsid protein molecules into virus-like particles and in the maintenance of the stability of the virus-like particles formed, with these hydrophobic groups being entrapped inside the normal virus-like particles. In solutions containing a high concentration of chaotropic agent, such as an urea solution or a guanidine hydrochloride solution, virus-like particles undergo partial or complete dissociation under the high concentration of chaotropic agent, resulting in the disruption of the higher structures of the proteins and the exposure (to solution) of the hydrophobic groups entrapped inside the normal virus-like particles. When the chaotropic agent is gradually removed from the solution, the interactions among the exposed hydrophobic groups increase more and more such that the denatured capsid proteins form aggregate particles. Fusion proteins in the solutions containing a high concentration of chaotropic agent, such as an urea solution or a guanidine hydrochloride solution, will also have the hydrophobic groups of their capsid proteins exposed to the solution. However, when the is chaotropic agent is gradually removed from the solution, the exposed hydrophobic groups of the capsid proteins are protected by the molecular chaperone proteins in the fusion proteins, so that the fusion proteins can be present in soluble form in the solution and undergo renaturation and self-assembly to finally form particulate immunogenic macromolecules. Fusion proteins are molecules distinct from capside proteins, mostly in that the process of such in vitro denaturation, renaturation and self-assembly of fusion protein molecules has completely different nature in terms of the surrounding conditions for the process, the factors involved in the process and the progression of the process, as compared with the process of the natural in vivo folding and self-assembly of capsid protein molecules. Therefore, the morphological characteristics of the macromolecule according to the present invention formed by in vitro denaturation, renaturation and self-assembly of fusion proteins are different from those of nature virus-like particles.

Although the immunogenic macromolecule according to the present invention does not have the morphological characteristics of nature virus-like particles, they still have a very strong immunogenicity. Such difference in the morphological characteristics may lead to that the antigens or antigen determinants exposed by the capsid proteins in the immunogenic macromolecule according to the present invention is different from those exposed by the capsid proteins in the virus-like particles. Since the organism's immune responses, especially humoral immune responses, have a close correlation with the exposed antigens or antigen determinants, the difference in the exposure of antigens or antigen determinants by the capsid protein molecules between the immunogenic macromolecule according to the present invention and the virus-like particles provides the following advantages:

1. The immune responses in the organisms induced by previous viral infections have no effect on the immunogenic macromolecule according to the present invention, therefore use of the immunogenic macromolecule according to the present invention as immunogen can avoid the the immune attack against viral capsid proteins in the organisms. In contrast, the virus-like particles are subjected to attack of the organism's immune responses such that they fail to serve as the immunogen to activate immune responses in the organism;

2. If the organisms develop immune tolerance to viral infection, the immunogenicity of the corresponding virus-like particles may be affected by the immune tolerance. The effect of this immune tolerance can be circumvented using the immunogenic macromolecules according to the present invention;

3. Use of the immunogenic macromolecules according to the present invention as immunogens can avoid the generation of interference to the immune analysis of commercially available capsid proteins.

The immunogenic macromolecules according to the present invention have a very strong immunogenicity, because: (1) they consist of a number of monomers or subunits, and they are in particulate form with a molecular weight of more than 1,000 KD, given that a particulate antigen is 1,000 or 10,000 times more immunogenic than a monomeric soluble antigen; and (2) some of the sequences of the capsid protein in the fusion protein may be recognized by the organism's innate immune mechanisms, which produces strong and persistent immune responses in combination with the organism's acquired immunity.

After being expressed by recombinant DNA technology, the fusion portion containing capsid proteins according to the present invention can be separated and purified in one or more steps using a high concentration of chaotropic agent, such as urea or guanidine hydrochloride. The purified fusion protein can undergo renaturation and self-assembly as the chaotropic agent is gradually removed to form the immunugenic macromolecules according to the present invention.

A method for preparing said immunugenic macromolecules includes: (1) culturing the cells comprising the nucleic acid that encodes said fusion protein, to express said fusion protein; (2) separating and purifying the fusion protein obtained from (1), wherein a chaotropic agent is used in one or more steps in the separation and purification process; and (3) allowing the fusion protein obtained from (2) to self-assemble into said immunogenic macromolecules by removing the chaotropic agent.

The chaotropic agent that can be used is selected from (but not limited to) urea or guanidine hydrochloride. The concentration of urea used may be in the range of 1-10 M, preferably in the range of 2-8 M. The concentration of guanidine hydrochloride used may be in the range of 1-10 M, preferably in the range of 1-6 M.

As the capsid protein in the fusion protein molecule undergoes self-assembly, the immunogenic macromolecules may be formed by packing the nucleic acid therein. Some nucleic acids, such as double-stranded RNA or non-methylated CpG-DNA, are strong immunostimulants and can significantly enhance the organism's immune responses.

The fusion protein according to the present invention, when separated and purified, can undergo renaturation and self-assembly to form immunogenic macromolecules (i.e. multi-molecule polymers) having a molecular weight of more than 1,000 KD. Said immunogenic macromolecules are in particulate form such that their immunogenicity is 1,000 or 10,000 times stronger than a monomeric soluble antigen. Test by molecular sieve column chromatography has shown that the position of the elution peak for the immunogenic macromolecules according to the present invention is essentially consistent with that for the virus-like particles formed by capsid proteins.

The present invention also provides the use of said immunogenic macromolecule in the manufacture of a composition for the prevention or treatment of the diseases associated with human papillomavirus (HPV) infection. Said diseases are selected from (but not limited to): tumors (such as cervical cancer, vaginal cancer, anal and perianal cancers, oropharyngeal cancer, maxillary sinus cancer, lung cancer), cervical intraepithelial neoplasia or external genital verrucae.

Composition

The present invention also provides an immunogenic composition (preventive or therapeutic vaccine) comprising an effective amount of said immunogenic macromolecules according to the present invention and a pharmaceutically acceptable carrier.

As used herein, "pharmaceutically acceptable" components refer to a substance suitable for use in human and/or mammal subjects without undue adverse side effects (such as toxicity), commensurate with a reasonable benefit/risk ratio. The term "pharmaceutically acceptable carrier" refers to a carrier for the administration of a therapeutic agent, including various excipients and diluents. This term refers to such carriers for therapeutic agents as are not per se the essential active components and are not unduly toxic after application. Suitable carriers are well-known to those of ordinary skill in the art. A full description of pharmaceutically acceptable carriers can be found in Reminton's Pharmaceutical Sciences (Mack Pub. Co., N.J. 1991). The pharmaceutically acceptable carriers in the composition may comprise liquids, such as water, saline, glycerol and sorbitol. Moreover, these carriers may have auxiliary agents, such as for example lubricating agent, glidant, wetting agent or emulsifying agent, pH buffering substance and stabilizing agent, e.g., albumin or the like.

Said composition can be formulated into various types of dosage suitable for administration to mammals, including but not limited to injections, capsules, tablets, emulsions, suppositories.

Animal experiments showed that mice immunized with the vaccine prepared using the immunogenic macromolecules according to the present invention had a decreased tumor growth rate and a reduced tumor volume, which effectively increased the survival rate of the tumor-bearing mice.

When intended for use, the immunogenic macromolecules according to the present invention are administered to the mammal subjects (such as human subjects) at a safe and effective amount, wherein said safe and effective amount is typically at least about 1 μg/kg body weight, and in most cases is not more than about 10 mg/kg body weight, preferably in the range of about 1 μg/kg body weight to about 1 mg/kg body weight. The particular dosage administered is, of course dependent on such considerations as the route of administration, the general health of the patient and the like, which are within the skill of medical practitioners.

The present invention is further described in conjunction with the following particular examples. It should be understood that these examples are illustrative of the present invention rather than limitative of the scope of the present invention. The experiment procedures in the following examples for which no particular conditions are specified generally follow those conditions such as described in Sambrook et al., Molecular Cloning: A Laboratory Manual, New York, Cold Spring Harbor Laboratory Press, 1989), or those conditions recommended by the manufacturers. Unless otherwise indicated, the percentages and parts are by weight.

Example 1

Design and Synthesis of the Gene for the FCCP Molecule Carrying HPV Antigen

The molecular chaperone protein used was derived from the Hsp65 of Mycobacterium bovis BCG (Thole J E, Keulen W J, De Bruyn J, Kolk A H, Groothuis D G, Berwald L G, Tiesjema R H, van Embden J D. 1987. Characterization, sequence determination, and immunogenicity of a 64-kilodalton protein of Mycobacterium bovis BCG expressed in Escherichia coli K-12. Infect. Immun. 55(6):1466-75; GeneBank accession number: M17705.1). The molecular chaperone protein was fused to the C-terminal of the capsid protein of hepatitis B virus (HBV) ADW2 subtype (core antigen, NCBI nucleotide accession number: AF324148) to form a fusion capsid-chaperone protein (FCCP) molecule. Human papillomavirus (HPV) type 16 E7 protein (GeneBank accession number: #K02718) was selected as the antigen to be carried. The E7 protein was fused to the N-terminal of the capsid protein molecule in FCCP to form a fusion protein of FCCP carrying the E7 antigen, which is E7-Core-Hsp65, whose amino acid sequence is shown in SEQ ID NO: 1.

The molecular weight of E7-Core-Hsp65 fusion protein was deduced to be 89.245 KD by its amino acid sequence. Based on sequences from GenBank, the DNA sequence encoding E7-Core-Hsp65 (also referred to as E7-Core-BCG65) fusion protein was prepared by total artificial synthesis using chemical methods. This synthesized DNA sequence, 2,479 bp in total, is as shown in SEQ ID NO:2 and named as Ankegens 2479 bp. It was cloned into pBluescript II SK (+/−)(Stratagene) vector at the SmaI site to obtain the recombinant plasmid pBSK-Ankegens-2479 bp (See FIG. 1).

Example 2

Recombinant Expression and Separation and Purification of E7-Core-Hsp65 Fusion Protein DNA fragments for E7-Core-BCG65 fusion protein were cleaved from plasmid pBSK-Ankegens-2479 bp by NdeI and EcoRI and then subcloned into the corresponding sites in the expression plasmid pET-23a (Emdbiosciences) to obtain the recombinant plasmid pET-23a-2479. This recombinant plasmid was transformed into the host bacteria Rosetta-gami (DE3) from Novagen for the expression of E7-Core-Hsp65 fusion protein. According to pET System Manual from Novagen, the E. coli strain Rosetta-gami(DE3) transformed with the recombinant plasmid was fermentatively cultured and induced with 0.5mM IPTG (isopropyl-thio-galactopyranoside) to achieve the expression of E7-Core-Hsp65 fusion protein. The SDS-PAGE electrophoregram of the expression product is shown in FIG. 2, in which lane 1 represents the electrophoresis result for the whole host bacteria Rosetta-gami(DE3) without recombinant plasmid, lanes 2, 3, 4 and 5 represent the electrophoresis results for the pET-23a-2479-transformed whole host bacteria Rosetta-gami(DE3) after IPTG induction, and lane 6 represents the electrophoresis result for the low molecular weight protein standard.

After fermentation, cells were harvested by centrifugation. 100 g of wet cells were suspended in 1,000 ml of Buffer A (100 mM Tris-HCl pH 9.0; 5 mM EDTA). The cells, when fully suspended, were centrifuged at 8,500 rpm for 30 minutes. The supernatant was discarded and the pellet was suspended in 1,000 ml of Buffer B (50 mM sodium acetate; 2 mM EDTA). The fully suspended cells were lysed by high-pressure homogenization at 760 bar and then the lysate was centrifuged at 8,500 rpm for 30 minutes. The supernatant was collected and the precipitate was discarded. Urea was added to the supernatant in a ratio of 0.7 g of urea per 1 ml of the supernatant. Then NaCl was added to a final concentration of 100 mM and L-Cysteine was added to a final concentration of 20 mM. The mixture was thoroughly stirred at room temperature, and when urea was completely dissolved, the resulting solution was stirred at 4° C. overnight. After overnight stirring, the sample was loaded to an XK-50 chromatography column (GE Health) containing 300 ml of SP-Sepharose (GE Health) as the packing material, which column was previously washed with 1 M of NaCl and sufficiently equilibrated with Buffer C (50 mM sodium acetate; 100 mM NaCl; 2 mM EDTA; 8 M urea; 10 mM L-Cysteine). After sample loading, the column was washed with 10 column volumes of Buffer D (50 mM sodium acetate; 100 mMNaCl; 2 mM EDTA; 8 M urea, 10 mM L-Cysteine; 2.5% Triton-X-100) overnight to remove endotoxin contamination. Subsequently, the column was washed with 5 column volumes of Buffer C to remove Triton-X-100, and then washed with 3 column volumes of Buffer E (50 mM sodium acetate; 300 mM NaCl; 2 mM EDTA; 8 M urea; 10 mM L-Cysteine) to remove other contaminants. E7-Core-BCG65 fusion protein was eluted from the column with Buffer H (50 mM sodium acetate; 800 mM NaCl; 2 mM EDTA; 8 M urea; 10 mM L-Cysteine). Pooled eluted protein was dialyzed against 4× 40 volumes of Buffer F (50 mM sodium acetate, 6 M urea) to remove NaCl and L-Cysteine. After dialysis, the dissociation of disulfide bonds were performed by adding sodium sulfite and sodium tetrathionate to final concentrations of 200 mM and 50 mM respectively, and incubating the mixture overnight at room temperature. Then the resultingsample was diluted with 5 volumes of Buffer F and the dilution was loaded to an XK-50 chromatography column containing 150 ml of Q-Sepharose (GE Health) as the packing material, which column was previously washed with 1M NaCl and sufficiently equilibrated with Buffer F. After sample loading, the column was washed with 2 column volumes of 95% Buffer F and 5% Buffer G (50 mM sodium acetate; 1 M NaCl; 6 M urea). Then E7-Core-BCG65 fusion protein was eluted with a linear gradient from 95% Buffer F and 5% Buffer G to 50% Buffer F and 50% Buffer G over 8 column volumes. Eluted E7-Core-BCG65 fusion protein was pooled, and then dialyzed against dialysis solution (1×40 volumes of Tris.HCl pH9.0, 1×40 volumes of Tris.HCl pH7.5 and containing 100 mM NaCl) to remove urea, and allowing E7-Core-BCG65 fusion protein to renature and self-assemble into multi-molecule polymer.

Figures 2, 3:
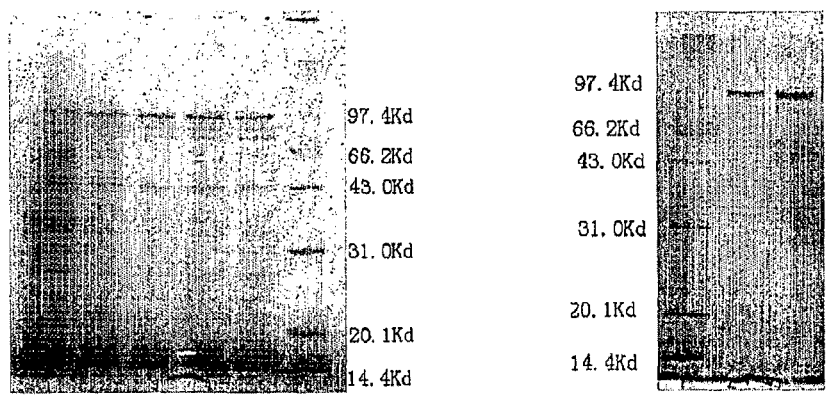
FIG. 2 is the 12% SDS-PAGE electrophoregram for the recombinantly expressed E7-Core-GcG65 in Example 2 of the present invention.
FIG. 3 is the SDS-PAGE electrophoregram for the separated and purified E7-Core-GcG65 fusion protein in Example 2 of the present invention.

The purity of the final separated and purified sample before dialysis was determined by SDS-PAGE electrophoresis, and the result showed that E7-Core-BCG65 fusion protein was manifested as a major band having a molecular weight of nearly 90 KD (see FIG. 3). In FIG. 3, lane 1 represents the electrophoresis result for the low molecular weight protein standard, lane 2 represents the electrophoresis result for E7-Core-BCG65 fusion protein with a loading amount of 0.8 μg, and lane 3 represents the electrophoresis result for E7-Core-BCG65 fusion protein with a loading amount of 1.7 μg.

Figure 4:
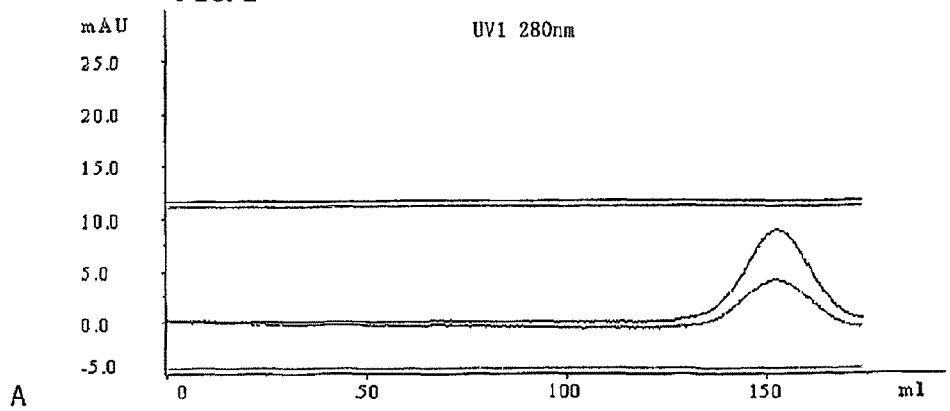
FIG. 4 compares the profiles of molecular sieve column chromatography in Example 2 of the present invention.

Test by molecular sieve column chromatography showed that the molecular weight of the renatured E7-Core-BCG65 as reflected by its elution peak was significantly larger than that of the corresponding monomeric protein (bovine serum albumin). The position of the elution peak of renatured E7-Core-BCG65 was essentially consistent with that of the virus-like particle formed from human papillomavirus 16 L1 major capsid protein, which suggests that the renatured E7-Core-BCG65 exhibits the characteristics of multi-molecule polymer (FIG. 4). In FIG. 4, panel A is the molecular sieve column chromatogram for bovine serum albumin (68 KD) having a protein concentration of 1.2 mg/ml, panel B is the molecular sieve column chromatogram for the renatured E7-Core-BCG65 according to the present invention having a protein concentration of 1.5 mg/ml, and panel C is the molecular sieve column chromatogram for the virus-like particle formed from human papillomavirus L1 having a protein concentration of 1.3 mg/ml. The basic parameters of molecular sieve column chromatography are as follows: column diameter, 1.6 cm; column length, 100 cm; packing material, Sepharose 4FF (GE Healthcare); amount of packing material loaded, 180 ml; mobile phase, 100 mM PB, 0.4 M NaCl, pH 6.5; velocity of flow, 2 ml/min; loading amount, 1 ml.

Electron microscopic observation showed that the typical morphological characteristics of the virus-like particle formed from human hepatitis B virus capsid proteins was absent in the multi-molecule polymer obtained in the present example. See FIG. 5, in which panel 5B has a larger magnification than panel 5A.

The multi-molecule polymer obtained in the present example was subjected to N-terminal amino acid sequencing, and the N-terminal amino acid sequence was determined to be MHGDTPTLHEYMLD, which is identical to the theoretical N-terminal sequence of E7-Core-BCG65. In conjunction with the SDS-PAGE result that the determined molecular weight of the separated and purified product was consistent with the expected molecular weight of E7-Core-BCG65 (FIG. 3), the multi-molecule polymer obtained in the present example was confirmed to consist of E7-Core-BCG65.

The multi-molecule polymer prepared in the present example was subjected to Western blotting analysis using the monoclonal antibody against hepatitis B virus core antigen from Abcam Corp. and it was found that the monoclonal antibody failed to recognize the core antigen in E7-Core-BCG65. Therefore the multi-molecule polymer prepared in the present example, when used as immunogen, may circumvent the immune attack against HBV capid protein (core antigen) in the organisms.

The final product prepared in the present example has an endotoxin content of below 5EU per milligram of protein.

Example 3

Determination of the Particle Size of the Multi-Molecule Polymer

The multi-molecule polymer prepared in Example 2 above mentioned was diluted about 3-fold using 50 mmol/L mops buffer +0.5 mol/L NaCl+0.03% Tween-80, pH 7.0. The particle size of the multi-molecule polymer was determined using Malvern Zetasizer Nano ZS (Marvern Instruments Ltd., England).

Conditions of determination: 25° C.; 3 min equilibrium time; water, used as the reference; DTS0012-Disposable sizing cuvette, used as the measuring cup; the determination is repeated in duplicate.

Figure 6:
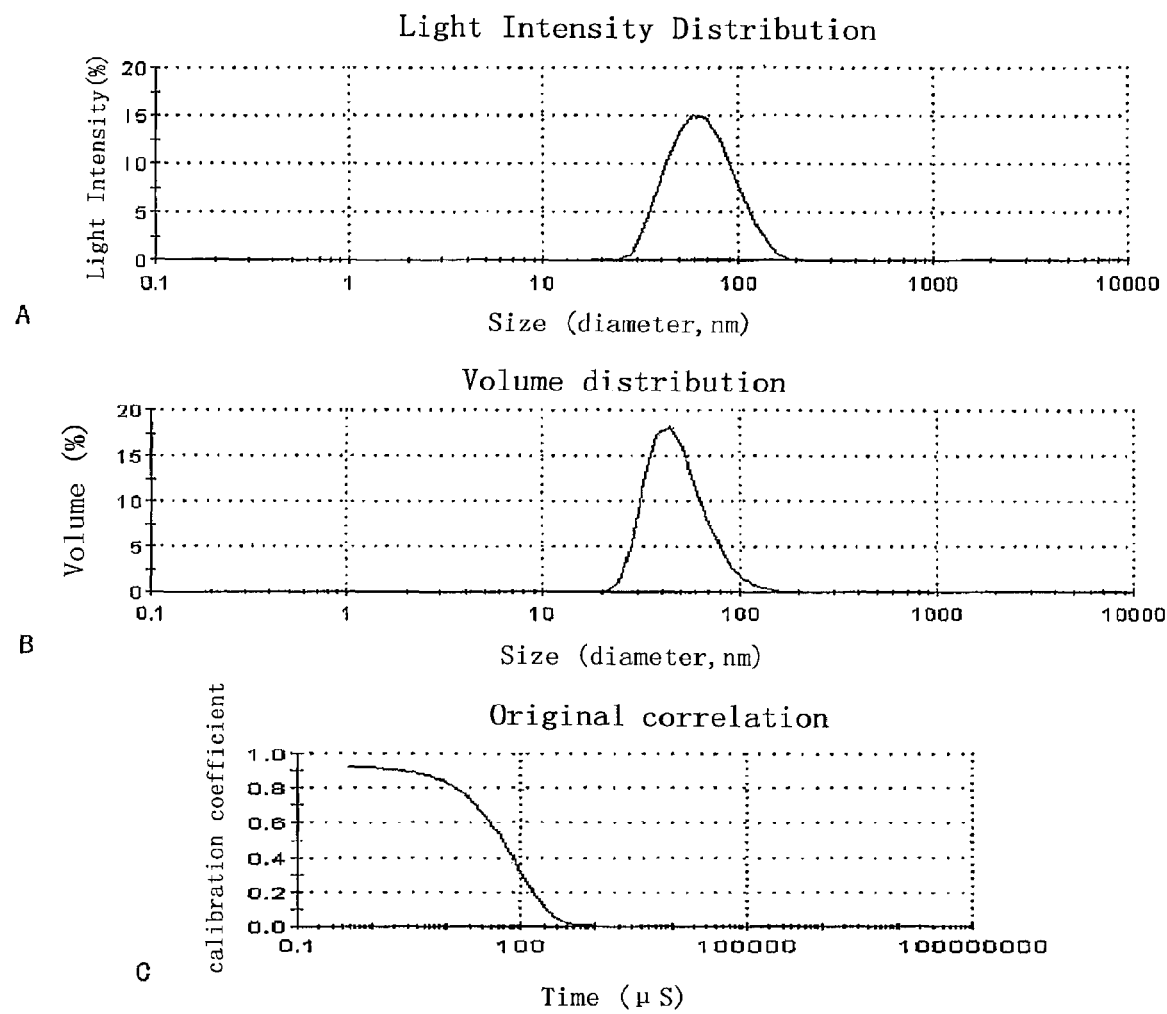
FIG. 6 shows the determinations of the particle size of the multi-molecule polymer, wherein A shows the light intensity distribution of the particles, B shows the volume distribution of the particles, and C shows the quality report of the determination results.

The results of determination are as shown in FIG. 6, in which A shows the light intensity distribution of the particles, B shows the volume distribution of the particles, and C shows the quality report of the determination results. It is known from the results that the multi-molecule polymer has a Z-Average size of 61.3 nm, and a PDI<0.2, thus the data of the determination is reliable.

Example 4

Therapeutic and Preventive Effects of Multi-Molecule Polymer Formed from E7-Core-BCG65 Fusion Protein in Animal Experiments The multi-molecule polymer formed from E7-Core-BCG65 fusion protein carries human papillomavirus 16 E7 antigen (E7 protein). In the present invention, the therapeutic and preventive effects of the multi-molecule polymer were evaluated in mice experiments using TC-1 tumor cell line that expresses E7 antigen.

Female C57BL/6 mice, six to eight weeks old (20.0±2.0 g) were purchased from Shanghai Slac Laboratory Animal Co. Ltd. (Quality Control No.: SCXK (Shanghai) 2003-0003).

TC-1 tumor cell line that expresses E7 antigen was derived from primary lung cells of C57BL/6 mice. The primary cell line was transformed by introducing the primary cell line with human papillomavirus 16 E7 gene and an activated human C-Ha-ras gene, and obtained the ability of immortalization.

The TC-1 cells were routinely grown in RPMI-1640 medium supplemented with penicillin/streptomycin, 2 mM L-glutamine, 1 mM sodium pyruvate, 2 mM nonessential amino acids, and 10% FBS. The well-grown in vitro TC-1 cells were harvested, washed three times with PBS, and adjusted to a cell density of $1\times10^5$ cells/ml. Each of the C57BL/6 mice was inoculated with 0.2 ml of the cells injected subcutaneously in the left flank. Then the mice were randomized into groups and administered the multi-molecule polymer according to the predetermined protocol. The sample of the multi-molecule polymer was diluted with saline and injected subcutaneously on the back of the mice. The animals were observed for tumor growth every day. The number of animals with tumor occurring at different times after injection was recorded, and tumor formation rate was calculated, that is, the ratio of the number of animals with tumor occurring to the number of actual animals in each group. When tumor became palpable, the long and short diameters of the tumors were measured using vernier caliper twice a week for calculation of tumor volume, that is, tumor volume=(long diameter×short diameter$^2$)/2. The survival time for each animal after tumor occurrence was recorded. Data were expressed in mean±SD ($\bar{X}$±s). The experimental animals were randomized into 6 groups (see table 2).

Subcutaneous tumor growth was observed 4 days after the C57BL/6 mice were inoculated with $1\times10^5$ TC-1 cells injected subcutaneously in the left flank. For the animals in Control group, tumor formation rate reached 100% in 10 days after inoculation. The tumors were even in size, with a volume of about 40 mm$^3$. The tumors grew so fast that the mean tumor volume of the Control group was 7499.84 mm$^3$ at day 36 after inoculating tumor cells. This group of animals began to die due to excess tumor burden 45 days after inoculation and all died by Day 60.

For the animals in the Therapeutic groups, they received the first immunization at 48 h after tumor inoculation (that is, received administration of the multi-molecule polymer prepared in Example 2) and then received boost immunization on Day 16. With immunization with the HPV therapeutic vaccine, the mice showed decreased tumor growth rate and reduced tumor volume. A dose-effect relationship was obvious among the groups of different doses. The mice in the Therapeutic groups all survived 60 days after tumor inoculation (see Table 2).

For the animals in the Preventive groups, they received two immunizations with an interval of 14 days followed by inoculation with tumor cells 14 days after the second immunization. With immunization with 100 μg or 20 μg of the polymer, the mice had a low tumor formation rate after tumor inoculation and they all survived 60 days after the inoculation (see Table 3).

TABLE 2

Animal experiment groups

| Groups | Number of mice | Dosage per mice | Administration time |
| --- | --- | --- | --- |
| Large dose, Therapeutic | 8 | 500 μg | First immunization at 48 h after inoculation, boost immunization on Day 16 |
| Medium dose, Therapeutic | 8 | 100 μg | First immunization at 48 h after inoculation, boost immunization on Day 16 |
| Small dose, Therapeutic | 8 | 20 μg | First immunization at 48 h after inoculation, boost immunization on Day 16 |
| Large dose, Preventive | 8 | 100 μg | Two immunizations with an interval of 14 days followed by inoculation with tumor cells 14 days after the second immunization |
| Small dose, Preventive | 8 | 20 μg | Two immunizations with an interval of 14 days followed by inoculation with tumor cells 14 days after the second immunization |
| Control | 6 | Saline | Administrated at 48 h after inoculation, time period as above |

TABLE 3

The average tumor volume in different experiment groups (mm³)
($\bar{X} \pm s$)

| Date (day) | Therapeutic Group | | | Preventive Group | | Control Group |
|---|---|---|---|---|---|---|
| | 500 µg (n = 8) | 100 µg (n = 8) | 20 µg (n = 8) | 100 µg (n = 8) | 20 µg (n = 8) | (n = 6) |
| 10 | 8.65 ± 5.40 | 16.33 ± 8.83 | 42.54 ± 24.55* | 2.32 ± 1.06 | 5.56 ± 2.91 | 39.00 ± 19.28 |
| 13 | 41.70 ± 20.90 | 51.01 ± 20.37 | 84.72 ± 36.72* | 1.97 ± 2.44 | 10.58 ± 25.56 | 133.57 ± 69.64 |
| 16 | 31.91 ± 12.26 | 49.96 ± 20.62 | 189.07 ± 91.07* | 1.97 ± 1.42 | 5.24 ± 2.08 | 320.20 ± 149.14 |
| 19 | 35.69 ± 10.52 | 156.28 ± 46.49 | 208.49 ± 85.46 | 2.85 ± 1.49 | 25.65 ± 10.43 | 782.65 ± 257.69 |
| 22 | 43.89 ± 21.13 | 224.71 ± 107.46 | 357.47 ± 159.47 | 2.44 ± 1.98 | 35.24 ± 80.41 | 1033.81 ± 594.12 |
| 25 | 109.04 ± 47.41 | 257.01 ± 107.19 | 756.40 ± 258.40 | 4.52 ± 2.78 | 17.38 ± 6.76 | 2414.19 ± 1201.87 |
| 28 | 127.68 ± 56.24 | 395.56 ± 128.72 | 892.54 ± 364.47 | 18.81 ± 5.42 | 69.63 ± 24.46 | 4432.67 ± 1824.46 |
| 31 | 156.12 ± 49.46 | 525.81 ± 152.94 | 1527.21 ± 510.46 | 20.57 ± 10.46 | 85.57 ± 25.85 | 6024.54 ± 2465.46 |
| 34 | 181.89 ± 75.53 | 671.34 ± 301.28 | 2048.57 ± 1050.57 | 22.42 ± 18.60 | 89.08 ± 43.09 | 7499.84 ± 3722.56 |
| 37 | 250.52 ± 120.59 | 785.69 ± 268.85 | 3051.65 ± 1253.32 | 56.83 ± 25.56 | 173.59 ± 89.41 | 9483.58 ± 4565.74 |
| 40 | 396.88 ± 208.12 | 921.87 ± 368.03 | 3887.08 ± 1889.08 | 59.81 ± 26.79 | 173.92 ± 86.39 | 13141.43 ± 5077.39 |

Example 5

Variant of E7-Core-BCG65 Fusion Protein

A variant of E7-Core-BCG65 fusion protein was constructed based on the amino acid sequence of E7-Core-BCG65 in Example 1. This variant, named as E7-Core-BCG65-M, is different from E7-Core-BCG65 in that: the amino acid in Position 8 was changed from Leu to Ile; the amino acid in Position 812 was changed from Val to Leu; and amino acids Asp Asp Asp Asp Lys were added between Positions 283 and 284. The encoding sequence of E7-Core-BCG65-M was prepared by total artificial synthesis using chemical methods and cloned into the pBluescript II SK (+/−)(Stratagene) vector at the SmaI site with the same procedure as in Example 1.

Recombinant expression and separation and purification of E7-Core-BCG65-M fusion protein were carried out using the same procedure as in Example 2, with the final result that E7-Core-BCG65-M formed into particulate multi-molecule polymer.

Animal experiments were performed with the multi-molecule polymer formed from E7-Core-BCG65-M using the same procedure as in Example 4, and it was found that the polymer significantly inhibited tumor cell growth.

All publications recited in the present application are herein incorporated by reference to the same extent as if each individual publication is specifically and individually indicated to be incorporated by reference. Moreover, it is to be understood that, upon reading the disclosure set forth herein, those skilled in the art can make various modifications and changes to the present invention without departing from the scope of the present invention, and these equivalents are intended to be within the scope of the present invention as defined in the appended Claims.

What is claimed is:

1. A multi-molecule polymer formed by denaturation and renaturation of a fusion protein comprising a human papillomavirus E7 antigen, a viral capsid protein, and a molecular chaperone protein, wherein the structure of said polymer is morphologically different from a virus-like particle of said capsid protein.

2. The multi-molecule polymer according to claim 1, characterized in that said fusion protein comprises, from the amino terminal to the carboxyl terminal, said human papillomavirus E7 antigen, said viral capsid protein and said molecular chaperone protein.

3. The multi-molecule polymer according to claim 1, characterized in that a linking peptide is included between said viral capsid protein and said molecular chaperone protein, said linking peptide having at least one protease cleavage site therein.

4. The multi-molecule polymer according to claim 1, characterized in that said viral capsid protein is a hepatitis B virus core antigen.

5. The multi-molecule polymer according to claim 1, characterized in that said molecular chaperone protein is selected from the group consisting of heat shock protein 65, heat shock protein 60, heat shock protein 70, heat shock protein 90, and heat shock protein 100.

6. The multi-molecule polymer according to claim 1, characterized in that:
 (a) said human papillomavirus E7 antigen is a protein comprising the sequence of amino acids from position 1 to 98 in SEQ ID NO: 1; or
 (b) said viral capsid protein is a protein comprising the sequence of amino acids from position 99 to 283 in SEQ ID NO: 1; or
 (c) said molecular chaperone protein is a protein comprising the sequence of amino acids from position 284 to 823 in SEQ ID NO: 1.

7. The multi-molecule polymer according to claim 1, having a molecular weight of more than 1,000 KD.

8. An immunogenic composition comprising the multi-molecule polymer according to claim 1 and a pharmaceutically acceptable carrier.

9. The immunogenic composition according to claim 8, further comprising an immunostimulant.

10. The immunogenic composition according to claim 9, wherein the immunostimulant is double-stranded RNA or non-methylated CpG-DNA.

11. A method for preparing the multi-molecule polymer according to claim 1, characterized in that said method comprises:
 (a) culturing cells to express a fusion protein comprising a human papillomavirus E7 antigen, a viral capsid protein, and a molecular chaperone protein;
 (b) separating and purifying the fusion protein obtained from (a), wherein a chaotropic agent is used in one or more steps in the separation and purification process; and
 (c) removing the chaotropic agent, thereby allowing the fusion protein obtained from (b) to self-assemble to form said multi-molecule polymer.

12. A method of inducing an immune response against human papillomavirus, characterized in that said method comprises administering to a subject an effective amount of the immunogenic composition of claim 8.

* * * * *